(12) United States Patent
Park et al.

(10) Patent No.: US 10,568,733 B2
(45) Date of Patent: Feb. 25, 2020

(54) ANTERIOR CABLE REGION SUPERIOR CAPSULE RECONSTRUCTIONS

(71) Applicant: ARTHREX, INC., Naples, FL (US)

(72) Inventors: Maxwell C. Park, Calabasas, CA (US); Thay Q. Lee, Long Beach, CA (US)

(73) Assignee: ARTHREX, INC., Naples, FL (US)

( * ) Notice: Subject to any disclaimer, the term of this patent is extended or adjusted under 35 U.S.C. 154(b) by 157 days.

(21) Appl. No.: 15/804,231

(22) Filed: Nov. 6, 2017

(65) Prior Publication Data

US 2018/0206977 A1 Jul. 26, 2018

Related U.S. Application Data (60) Provisional application No. 62/449,621, filed on Jan. 24, 2017.

(51) Int. Cl.
| | |
|---|---|
| *A61F 2/08* | (2006.01) |
| *A61F 2/40* | (2006.01) |
| *A61B 17/04* | (2006.01) |
| *A61B 17/32* | (2006.01) |
| *A61B 17/16* | (2006.01) |
| *A61B 17/56* | (2006.01) |

(52) U.S. Cl.
CPC .............. *A61F 2/0811* (2013.01); *A61F 2/08* (2013.01); *A61B 17/0401* (2013.01); *A61B 17/16* (2013.01); *A61B 17/32* (2013.01); *A61B 17/320016* (2013.01); *A61B 2017/0404* (2013.01); *A61B 2017/044* (2013.01); *A61B 2017/564* (2013.01); *A61F 2002/0888* (2013.01)

(58) Field of Classification Search
CPC ...... A61F 2/08; A61F 2/0811; A61B 17/0401; A61B 2017/564
See application file for complete search history.

(56) References Cited

U.S. PATENT DOCUMENTS

| | | |
|---|---|---|
| 6,517,578 B2 | 2/2003 | Hein |
| 6,648,903 B1 | 11/2003 | Pierson, III |
| 6,666,877 B2 | 12/2003 | Morgan et al. |
| 7,329,272 B2 | 2/2008 | Burkhart et al. |

(Continued)

FOREIGN PATENT DOCUMENTS

| | | |
|---|---|---|
| WO | WO0013601 A1 | 3/2000 |
| WO | WO2009113076 A1 | 9/2009 |
| WO | WO2010030714 A2 | 3/2010 |

OTHER PUBLICATIONS

F. Hamido, et al., "The use of the LARS artificial ligament to augment a short or undersized ACL hamstrings tendon graft," The Knee, 2010 Elsevier B.V., doi: 10.1016/j.knee.2010.09.003.

(Continued)

*Primary Examiner* — Brian A Dukert
(74) *Attorney, Agent, or Firm* — Carlson, Gaskey & Olds (57) ABSTRACT

This disclosure details methods for improving the joint kinematics of an unstable joint. An exemplary method includes reconstructing an anterior cable region of a superior capsule of a glenohumeral joint. The anterior cable region may be reconstructed by fixating a graft at a greater tuberosity of a humerus to stabilize a glenohumeral joint. The graft is generally localized at the anatomical attachment site of the native anterior cable of the superior capsular ligament and extends from a superior glenoid to an anatomical attachment site of the native capsule or anterior cable. The graft can be an autograft or an allograft.

20 Claims, 8 Drawing Sheets

(56) References Cited

U.S. PATENT DOCUMENTS

| | | | |
|---|---|---|---|
| 8,231,653 | B2 | 7/2012 | Dreyfuss |
| 8,439,976 | B2 | 5/2013 | Klbertorio et al. |
| 8,460,379 | B2 | 6/2013 | Albertorio et al. |
| 8,597,336 | B2 | 12/2013 | van der Burg et al. |
| 8,668,718 | B2 | 3/2014 | Euteneuer et al. |
| 8,690,960 | B2 | 4/2014 | Hotter et al. |
| 8,764,798 | B2 | 7/2014 | Housman |
| 8,771,316 | B2 | 7/2014 | Denham et al. |
| 8,808,374 | B2 | 8/2014 | Eggli |
| 8,852,250 | B2 | 10/2014 | Lombardo et al. |
| 8,986,347 | B2 | 3/2015 | Housman |
| 9,113,977 | B2 | 8/2015 | Euteneuer et al. |
| 9,168,124 | B2 | 10/2015 | Guerra et al. |
| 9,271,826 | B2 | 3/2016 | Eggli et al. |
| 9,289,285 | B2 | 3/2016 | Eggli |
| 9,357,990 | B2 | 6/2016 | Ferguson et al. |
| 2008/0027470 | A1 | 1/2008 | Hart et al. |
| 2008/0188936 | A1 | 8/2008 | Ball et al. |
| 2009/0156997 | A1 | 6/2009 | Trenhaile |
| 2009/0222039 | A1 | 9/2009 | Dreyfuss et al. |
| 2010/0324676 | A1 | 12/2010 | Albertorio et al. |
| 2012/0265219 | A1 | 10/2012 | Rushdy et al. |
| 2013/0289574 | A1 | 10/2013 | Shinde |
| 2014/0155937 | A1 | 6/2014 | Shinde |
| 2015/0297338 | A1 | 10/2015 | Ammann |
| 2016/0113643 | A1 | 4/2016 | Diduch et al. |

OTHER PUBLICATIONS

Tamara J. Nancoo, et al., "TransMedial All-Inside Posterior Cruciate Ligament Reconstruction Using a Reinforced Tibial Inlay Graft," Artrhroscopy Techniques, vol. 2, No. 4 Nov. 2013; pp. e381-e388.

ACL Reconstruction with LARS Liagament Surgical Technique, 2009 Colin P No. 1931 Rev 0 May 2009 ECR 8843.

Robert Fridman, et al., Augmented Brostrom Repair Using Biologic Collagen Implant: Report on 9 Consecutive Patients, The Foot & Ankle Journal 1 (7): 4, 2008, ISSN 1941-6806.

Adam T. Groth, et al., "Lateral Ankle Ligament Injuries in Athletes: Diagnosis and Treatment," Operative Techniques in Sports Medicine, 2010 Elsevier Inc., doi:10.1053/j.otsm.2009.11.005.

R.K. Kdolsky, et al., "Braided Polypropylene Augmentation Device in Reconstructive Surgery of the Anterior Cruciate Ligament: Long-Term Clinical Performance of 594 Patients and Short-Term Arthroscopic Results, Failure Analysis by Scanning Electron Microscopy, and Synovial Histomorphology," Journal of Orthopaedic Research, 15:1-10 The Journal of Bone and Joint Surgery, Inc.k, 1997 Orthopaedic Research Society.

Claudio Legnanti, et al., "Anterior cruciate ligament reconstruction with synthetic grafts. A review of literature," International Orthopaedics (SICOT) (2010) 34:465-471, DOI 10.1007/s00264-010-0963-2.

Zuzana Machotka, et al., "Anterior cruciate ligament repair with LARS (ligament advanced reinforcement system): a systematic review," Sports Medicine, Arthroscopy, Rehabilitation, Therapy & Technology 2010, 2:29, http://www.smartjournal.com/content/2/1/29.

Peter J. Millett, "Arthroscopic Superior Capsular Reconstruction (ASCR) Procedure," http://drmillett.com/massive-rotator-cuff-tear-ascr-arthroscopic-superior. . .

Meca fix Juge Yvon Gautier, Augmented construct used clinically, Augmented construct mechanical testing, Non augmented construct.

Teruhisa Mihata, et al., Clinical Results of Arthroscopic Superior Capsule Reconstruction for Irreparable Rotator Cuff Tears, Arthroscopy: The Journal of Arthroscopic and Related Surgery, vol. 29, No. 3 Mar. 2013: pp. 459-470.

John-Paul H. Rue, et al., "Minimally Invasive Medial Collateral Ligament Reconstruction Using Achilles Tendon Allograft," Techniques in Knee Surgery 6(4):266-273, 2007.

Teruhisa Mihata, et al., Superior Capsule Reconstruction to Restore Superior Stability in Irreparable Rotator Cuff Tears: A Biomechanical Cadaveric Study, The American Journal of Sports Medicine, vol. 40, No. 10; DOI: 10.1177/0363546512456195.

ANTERIOR CABLE REGION SUPERIOR CAPSULE RECONSTRUCTIONS

CROSS-REFERENCE TO RELATED APPLICATIONS

This disclosure claims priority to U.S. Provisional Application No. 62/449,621, which was filed on Jan. 24, 2017, the entire disclosure of which is incorporated herein by reference.

BACKGROUND

This disclosure relates to methods for reconstructing portions of capsular ligaments of glenohumeral joints.

Normal joint kinematics are achieved through balanced soft tissues that surround the articulating bones of a joint. An unstable joint occurs if there is significant disruption of the articulating bones or the surrounding soft tissues. For example, rotator cuff tears may be accompanied by underlying capsular ligament tears that ultimately result in instability of the glenohumeral joint. This instability can cause pain, dysfunction, accelerated bone loss, soft tissue tears, premature arthritis, etc. When the rotator cuff is repaired, and the repair is only partial (for example, leaving a residual defect) or non-anatomical (for example, medialized), the repaired tendon must function as both a tendon and a ligament given the unique normal relationship between the tendon and underlying ligamentous capsule.

SUMMARY

This disclosure details methods for improving the joint kinematics of an unstable joint. The unstable joint may be stabilized by repairing or reconstructing portions of a capsular ligament of the joint.

An exemplary method includes reconstructing an anterior cable region of a superior capsule of a glenohumeral joint. As used herein, the term "anterior" is in relation to a repaired tendon or residual tendon tear or defect. In some embodiments, the method includes fixating a graft at a greater tuberosity of a humerus to stabilize a glenohumeral joint. The graft is generally localized at the anatomical attachment site of the native anterior cable of the superior capsular ligament and extends from a superior glenoid to an anatomical attachment site of the native capsule or anterior cable. The graft can be an autologous proximal long head biceps tendon, which is already attached proximally on the medial superior glenoid. The humeral attachment site would include, but is not limited to, an area anterior to any partial rotator cuff tendon repair or residual tendon tear or defect at the articular margin (i.e., the normal insertion region for the superior capsule of the glenohumeral ligament).

Another exemplary method includes harvesting a graft from a long head biceps tendon. The graft is harvested without detaching the long head biceps tendon from its superior glenoid attachment site. The graft is fixated at a greater tuberosity of a humerus to stabilize a glenohumeral joint. The graft is localized at an anterior cable region of a superior capsular ligament.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

The various features and advantages of this disclosure will become apparent to those skilled in the art from the following detailed description. The drawings that accompany the detailed description can be briefly described as follows.

DETAILED DESCRIPTION

This disclosure describes methods for reconstructing portions of a capsular ligament. The proposed methods are designed to improve the joint kinematics of an unstable joint and protect or internally support adjacent rotator cuff tendons.

An exemplary method includes reconstructing an anterior cable region of a superior capsular ligament of a glenohumeral joint. A graft may be used to reconstruct the anterior cable region. The graft may be either an autograft or an allograft. One end of the graft may be localized at or near the anatomical attachment site of the native anterior cable, and thus the method may be performed without reconstructing an entirety of the superior capsular ligament.

In some embodiments, the local autologous proximal long head biceps tendon is employed as the graft. The graft may be secured to the anatomical distal attachment site of the native capsule on the greater tuberosity articular margin, while the proximal portion is left in situ. In this way, the native biceps tendon tissue functions as a supporting ligament that supports not only the local rotator cuff tendon tissue, but local ligament tissue as well, thereby helping to maintain and sustain normal glenohumeral kinematics. These and other features are described in greater detail in the following paragraphs of this detailed description.

Figure 1:
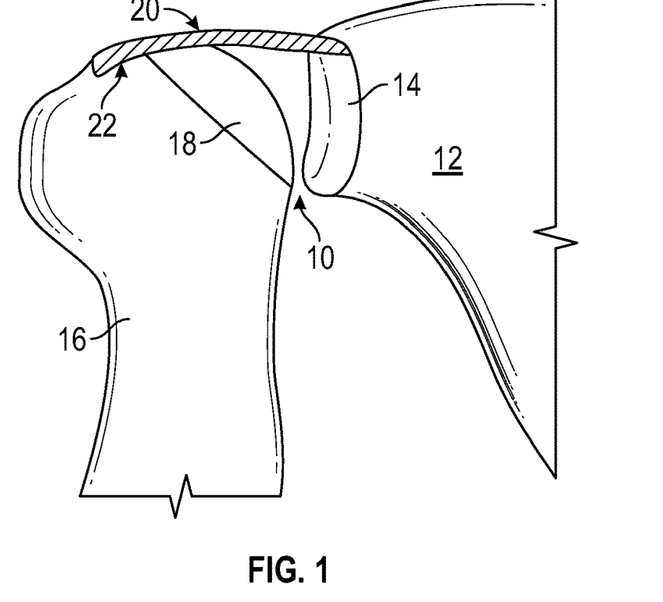
FIG. 1 illustrates a joint of a human musculoskeletal system.

FIG. 1 illustrates a joint 10 of the human musculoskeletal system. The joint 10 may be any joint of the musculoskeletal system of the human body. In an embodiment, the joint 10 is a glenohumeral joint of a human shoulder. The joint 10 is made up of multiple bones including a scapula 12 and a humerus 16. Some of these bones articulate relative to one another. For example, the joint 10 includes a ball and socket joint formed between a head 18 of the humerus 16 and a glenoid 14, which is a cup-like recession of the scapula 12 that receives the head 18.

A superior capsular ligament 20 generally covers the superior aspects of the joint 10 and is surrounded and reinforced by various muscles, tendons and ligaments that are responsible for keeping the adjoining bones of the joint 10 together. The joint 10 may become unstable if there is significant disruption of the articulating bones (e.g., the humerus 16 and the glenoid 14), the superior capsular ligament 20, or other surrounding muscles, tendons, and/or ligaments.

For example, a rotator cuff tear may render the joint 10 unstable. There is typically an obligatory underlying tear in the superior capsular ligament 20 when a rotator cuff tear occurs. The entirety of the superior capsular ligament 20 may need to be reconstructed to address massive, irreparable rotator cuff tears. However, for tears that are repairable to any degree, an anterior cable region 22 (i.e., the anterior aspect of the superior capsular ligament 20) alone can be reconstructed as opposed to the entirety of the superior capsular ligament 20 in order to augment and support the rotator cuff repair, and local capsule ligament, so that the tendon need not function as both a tendon and ligament, thus improving longevity of the rotator cuff repair and improving the joint kinematics and function of the glenohumeral joint. This disclosure therefore describes exemplary methods for reconstructing an anterior cable region 22 of the superior capsular ligament 20 to improve the joint kinematics of the joint 10. The term "anterior" is in relation to a repaired tendon or residual tendon tear or defect.

FIGS. 2-6, with continued reference to FIG. 1, schematically illustrate an exemplary method of reconstructing the anterior cable region 22 of the superior capsular ligament 20 of the glenohumeral joint 10. As detailed below, the exemplary method may be employed to prepare, deliver, and fixate a graft within the glenohumeral joint 10 in a manner that improves joint kinematics and functionality. As used herein, the term "joint kinematics" generally refers to the manner in which the bones and surrounding soft tissue of a joint interact with one another during motion.

Although schematically depicted, the method of FIGS. 2-6 may be performed as an arthroscopic procedure by working through various arthroscopic portals. Alternatively, the exemplary method could be performed as an open procedure.

Figure 2:
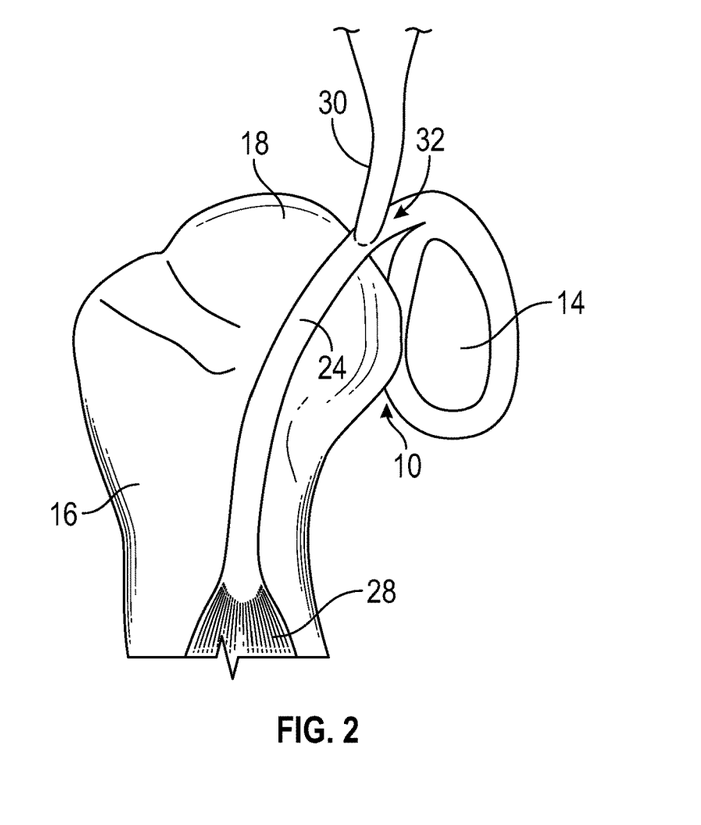
FIG. 2 schematically illustrates the passing of a flexible strand through a graft as part of an exemplary method of reconstructing an anterior cable region of a superior capsular ligament of a glenohumeral joint.

In an embodiment, the graft that is used to reconstruct the anterior cable region 22 is an autograft that may be locally derived from a long head biceps tendon 24. The long head biceps tendon 24 is schematically illustrated in FIG. 2. As is known, the long head biceps tendon 24 extends over the humeral head 18 and attaches to the superior aspect of the glenoid 14 in order to connect the biceps muscle 28 to the bones of the shoulder.

As shown in FIG. 2, a surgeon may initiate the anterior cable region 22 reconstruction method by passing one or more flexible strands 30 (e.g., suture) through or around a proximal portion 32 of the long head biceps tendon 24. The flexible strand(s) 30 may subsequently be used to fixate the graft that is locally derived from the long head biceps tendon 24 to the humerus 16, as discussed in greater detail below. The fixation locations of the flexible strand(s) 30 may be selected based on a surgeon's preference and are selected to best restore the anatomy and joint kinematics of the joint being repaired. The flexible strands 30 may include individual suture strands, multiple suture strands, suture tape, or any other suture-like product, including but not limited to simple or interlocking suture loop configurations.

Figure 3A:
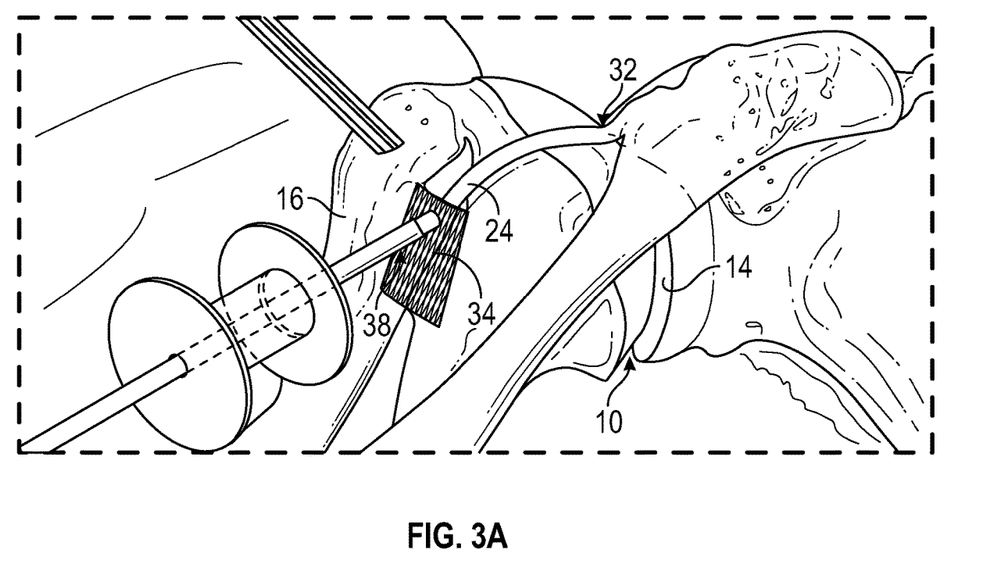
FIGS. 3A and 3B schematically illustrate exposing portions of the graft of FIG. 2.
Figure 3B:
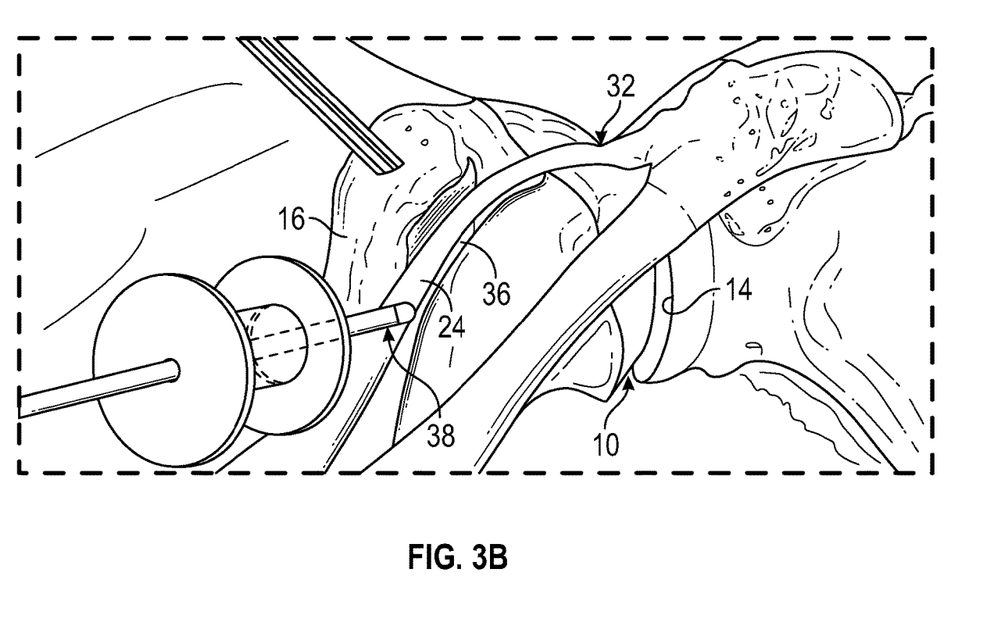

Next, as shown in FIGS. 3A and 3B, the proximal portion 32 of the long head biceps tendon 24 is exposed at the rotator cuff interval. If necessary, this step may include releasing a transverse ligament 34 (best shown in FIG. 3A). Releasing the transverse ligament 34 exposes the bicipital groove 36 (best shown in FIG. 3B) of the humerus 16 and thus enables adequate access to the proximal portion 32 of the long head biceps tendon 24. A cutting instrument 38 may be inserted into the operative field for releasing the transverse ligament 34. The cutting instrument 38 may be any suitable tissue cutting instrument.

The time at which the transverse ligament 34 is released during the method relative to when the flexible strands 30 are passed through or around the proximal portion 32 of the long head biceps tendon 24 could vary and is left to surgeon preference. For example, the proximal portion 32 of the long head biceps tendon 24 may be released (immediately after releasing the transverse ligament 34) just prior to fixation of the distal end of the graft laterally on the humerus 16, but after each of the medial flexible strands have all been secured.

Figure 4:
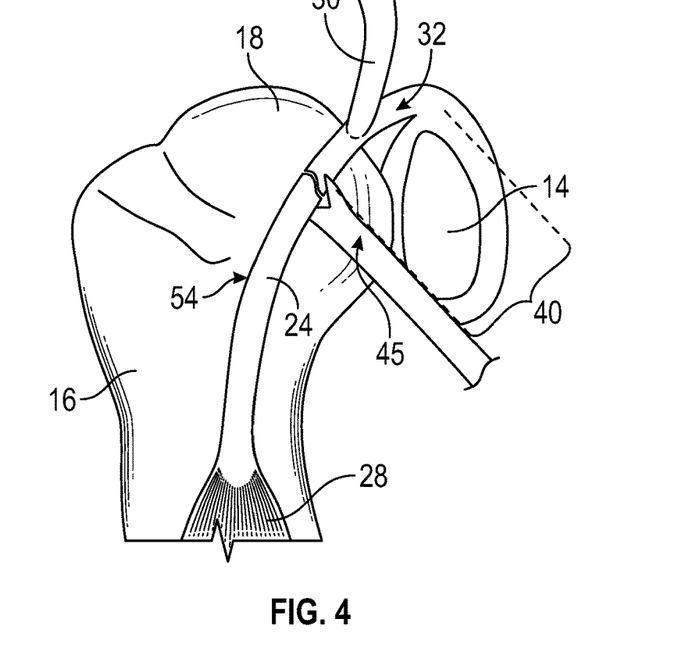
FIG. 4 schematically illustrates performing a tenotomy on the graft shown in FIGS. 2, 3A, and 3B.

Referring now to FIG. 4, a tenotomy is next performed to resect the long head biceps tendon 24 into the proximal portion 32 and a distal portion 54. The resection may be made using another cutting instrument 45, such as surgical scissors or any other suitable tissue cutting device. In an embodiment, the resection is made at a location distal to the labrum-tendon transition (i.e., not at the biceps tendon-superior labrum transition). In another embodiment, the resection is made at a location distal to the location where the flexible strand(s) 30 has been passed through the proximal portion 32 of the long head biceps tendon 24. The purpose of placing flexible strands through the tendon 24, versus around the tendon 24, include but are not limited to controlling the position of the tendon 24 after it has been tenotomized, if the tenotomy is performed prior to any definitive reconstruction fixation techniques.

Resecting the long head biceps tendon 24 in the manner described in the previous paragraph establishes a graft 40 that can subsequently be used to reconstruct any relative anterior cable region 22 of the superior capsular ligament 20. The graft 40 is essentially the section of the long head biceps tendon 24 that extends from its attachment point at the superior glenoid 14 to the location of the resection. Therefore, the proximal portion 32 of the long head biceps tendon 24 should be resected in a manner that allows for sufficient remaining length to reach and engage the greater tuberosity of the humerus 16 for reconstructing any relative anterior cable region 22.

Figure 5:
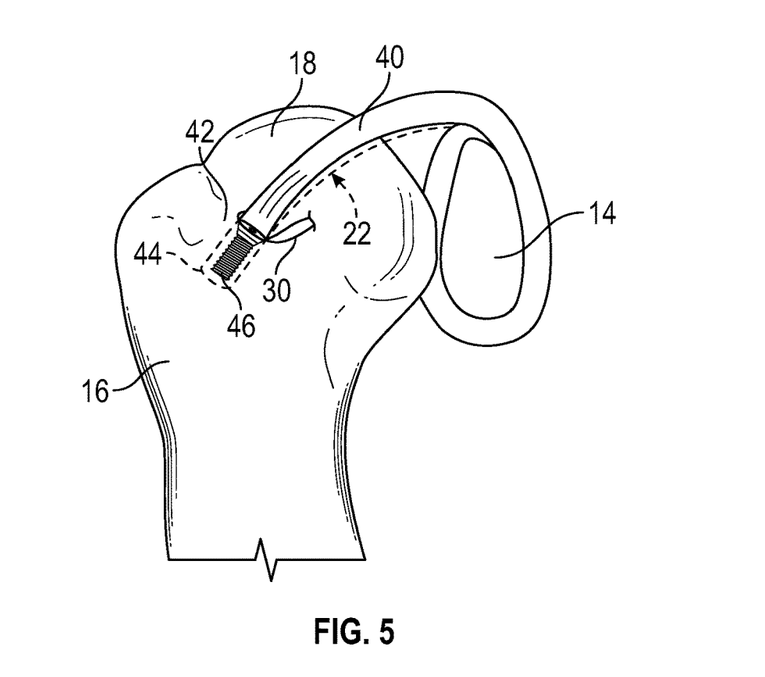
FIG. 5 schematically illustrates the fixation of a distal aspect of a proximal portion of the graft of FIGS. 2, 3A, 3B, and 4.

FIG. 5 illustrates the graft 40 after it has been fixated to the greater tuberosity 42 of the humerus 16. A socket 44 may first be formed in the greater tuberosity 42, such as at an anatomic attachment region of the normal superior capsule. The socket 44 may be formed in the greater tuberosity 42 such that when the graft 40 is affixed it extends along the anatomical attachment site of the native anterior cable region 22 (shown schematically with dashed line). In other words, rather than reconstructing the entirety of the superior capsular ligament 20, the exemplary method reconstructs only the anterior cable region 22 of the superior capsular ligament 20 by localizing the graft 40 at an anatomical attachment site of the superior capsule on the greater tuberosity 42 of the humerus 16.

A fixation device 46 (e.g., a suture anchor, a button, a screw, etc.) may be secured in the socket 44 to fixate a distal aspect of the graft 40 to the capsular attachment region of the greater tuberosity 42. In an embodiment, the flexible strand(s) 30 may be used in combination with the fixation device 46 to achieve adequate tension on the graft 40 during implantation of the fixation device 46. In another embodiment, the fixation device 46 is a knotless device that traps the graft between a sidewall of the socket 44 and a body of the fixation device 46. The SwiveLock®, which is sold by Arthrex, Inc., is a non-limiting example of one type of knotless anchor that may be suitable for knotlessly fixating the graft 40.

Notably, the fixation point is not limited to a socket, and may involve a tunnel, for example. Further, fixation to an attachment site on the greater tuberosity 42 may include compressive fixation (on-top position) and not necessarily involving a socket or tunnel into where the graft 40 occupies or traverses. In the case of the on-top position of the greater tuberosity, fixation may also occur distal-lateral to the tuberosity edge using various fixation devices. A trough may also be created on-top of the tuberosity to receive the graft in order to increase the surface area for healing.

Because the graft 40 is disassociated from the biceps muscle 28 during the resection step, it functions solely as a ligament once fixated to the greater tuberosity 42. Thus, the graft 40 stabilizes the humerus 16 and the glenoid 14 relative to one another, thereby improving joint stability and kinematics. Therefore, once the rotator cuff is subsequently repaired, or a defect is left with or without repair, the rotator cuff may function solely as a tendon rather than both a tendon and a ligament. Because the tendon is both supported by the reconstruction and need not function as a ligament, the tendon repair may be maintained and sustained for a longer duration of time compared to a tendon repair that does not have such support or autologous bracing. Further support can be derived from providing side-to-side fixation between the graft 40 and residual local capsular tissue. In this case, the graft 40 is supporting the local ligament as well as the tendon. Side-to-side fixation may include, but is not limited to, fixation around (compared to through) the graft 40. Suture can be used to achieve side-to-side fixation through or around the graft 40.

Figure 6:
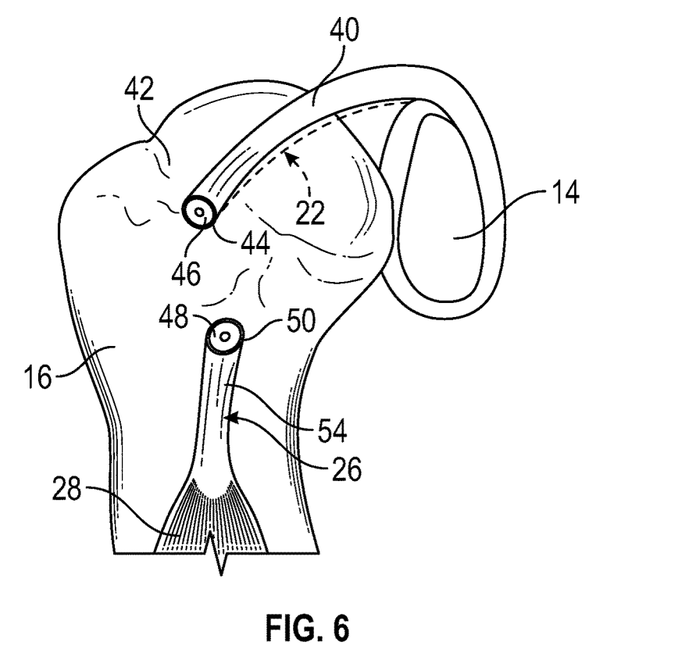
FIG. 6 schematically illustrates the fixation of the proximal aspect of a distal portion of the graft of FIGS. 2, 3A, 3B, 4, and 5.

Finally, as shown in FIG. 6, a proximal aspect of the distal portion 54 of the biceps tendon 26 may optionally be fixated to the humerus 16. This may include performing a standard biceps tenodesis procedure. In an embodiment, fixation of the proximal aspect of the distal portion 54 of the biceps tendon 26 may be achieved using a second fixation device 48 that is secured in a second socket 50 formed in the humerus 16.

Figure 7:
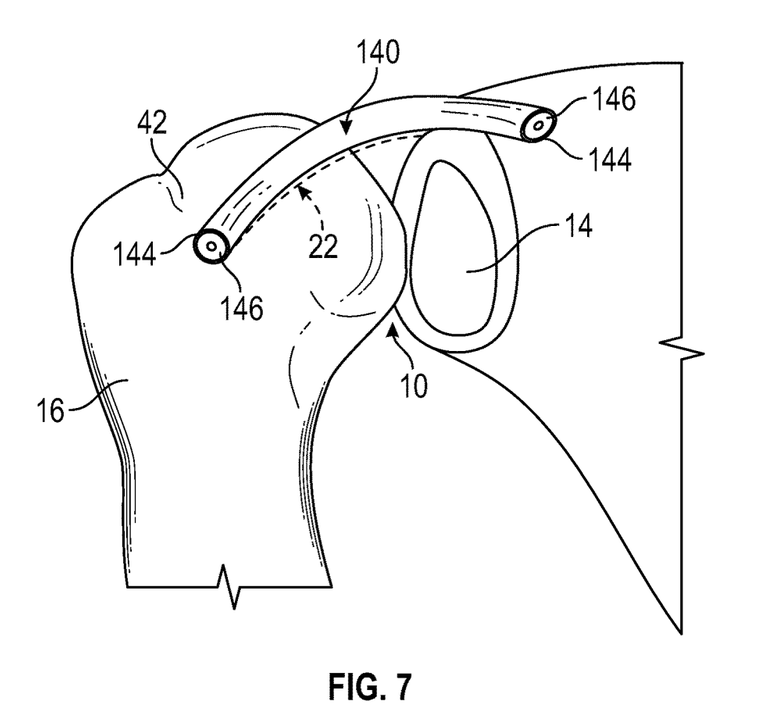
FIG. 7 schematically illustrates another exemplary method of reconstructing an anterior cable region of the superior capsular ligament of the glenohumeral joint.

FIG. 7, with continued reference to FIG. 1, schematically illustrates another exemplary method for reconstructing the anterior cable region 22 of the superior capsular ligament 20. A graft 140 may be used to reconstruct the anterior cable region 22. In the illustrated embodiment, the graft 140 is an allograft rather than an autograft, although an autograft could also be used in the manner depicted in FIG. 7.

The graft 140 is attached on both the glenoid side and the humeral side of the glenohumeral joint 10. For example, the graft 140 may be affixed to both the glenoid 14 and the humerus 16 using one or more fixations devices 146. The fixation devices 146 may trap the graft 140 within sockets 144 formed in the humerus 16 and the glenoid 14. The graft 140 could alternatively be fixated on top of the attachment sites, based on the type of anchor used, as another possible method. In an embodiment, the graft 140 can be fixated at the level or region of the anterior superior capsule/posterior rotator interval on the glenoid 14 and at the greater tuberosity 42 of the humerus 16. The graft 40 is therefore localized at the anatomical attachment site of the native superior capsule and extends between the glenoid and the humeral anatomical attachment sites.

FIGS. 8-15 schematically illustrate yet another exemplary method of reconstructing an anterior cable region of a glenohumeral superior capsular ligament. As detailed below, the exemplary method may be employed to prepare, deliver, and fixate a graft within the glenohumeral joint in a manner that improves joint kinematics and functionality. For example, rotator cuff defects may be supported using an autologous tendon graft cable that is repurposed as a ligament cable to stabilize the bones of the glenohumeral joint.

FIGS. 8 through 15 illustrate, in sequential order, the steps for performing an exemplary anterior cable region reconstruction. It should be understood; however, that fewer or additional steps than are recited below could be performed and that the recited order of steps is not intended to limit this disclosure.

A graft 240 is used to reconstruct the anterior cable region 22 of the glenohumeral joint 10. In an embodiment, the graft 240 is an autograft that may be locally derived from a long head biceps tendon. The long head biceps tendon may be harvested in a manner similar to that illustrated in FIGS. 2-4. The graft 240 is essentially the section of the long head biceps tendon that extends from its attachment point at the superior glenoid 14 to the location of the tendon resection.

Figure 8:
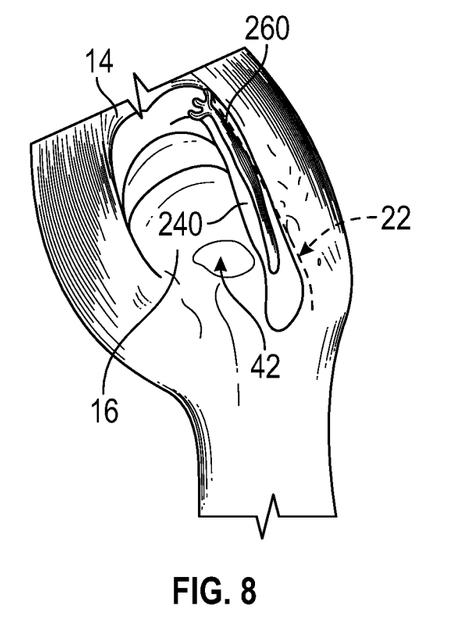
FIG. 8 schematically illustrates reinforcing a graft as part of another exemplary method of reconstructing an anterior cable region of a superior capsule.

As shown in FIG. 8, a reinforcement material 260 may optionally be secured to the graft 240 after the graft 240 has been harvested. The reinforcement material 260 may include any shape, size, and/or geometry for reinforcing the graft 240. The reinforcement material 260 increases the strength of the graft 240, thereby providing improved fixation.

The reinforcement material 260 may be secured to the graft 240 in any manner. For example, the reinforcement material 260 could be sutured to, looped around, or knotlessly fixated to the graft 240. The reinforcement material 260 may be any reinforcing material such as suture, tape, weave, mesh, or any combination of these materials. In an embodiment, the reinforcement material 260 is a synthetic mesh. Notably, based on the material configuration, the reinforcement material 260 may be secured either before or after graft tenotomy.

Figure 9:
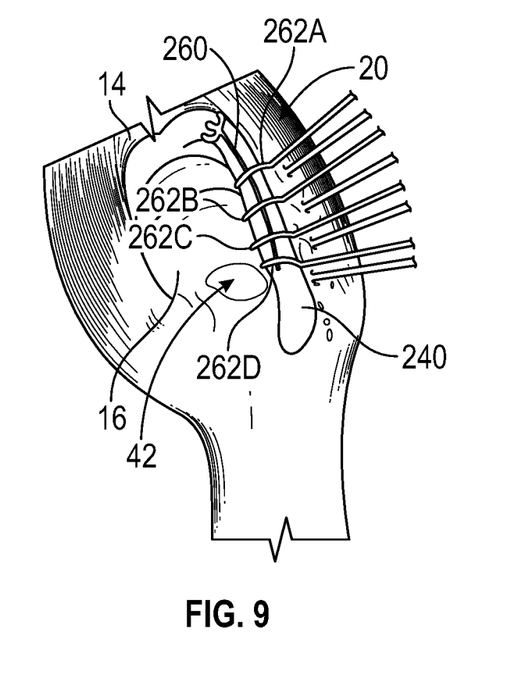
FIG. 9 schematically illustrates the placement of various sutures around the graft of FIG. 8.

Referring next to FIG. 9, various sutures 262A-262D may be passed into the joint space and positioned relative to the graft 240 to prepare the graft 240 for fixation to the intact portions of the native superior capsular ligament 20 and the humerus 16. The sutures 262A-262D may be positioned around the graft 240 as opposed to through it in order to avoid reducing the structural integrity of the graft 240. Any number of sutures 262A-262D may be used to secure the graft 240 in place in the joint. Accordingly, the amount of sutures shown in the various figures should not be interpreted as limiting this disclosure in any manner.

The sutures 262A-262D may include individual suture strands, multiple suture strands, suture tape, knotless sutures, or any other suture-like product or combinations of suture-like products. In an embodiment, as discussed in further detail below, at least a portion of the sutures 262A-262D are configured as knotless suture constructs that can be cinched around graft or other tissue to knotlessly secure the graft/tissue relative to bone or between soft tissue (e.g., graft and native capsule defect).

Figure 10:
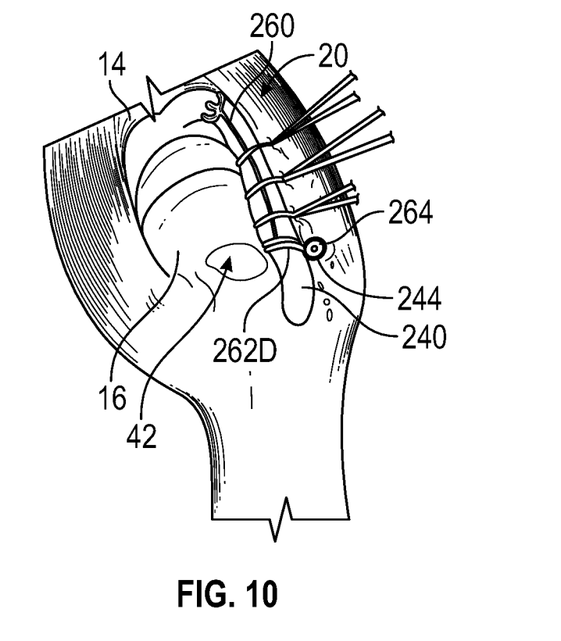
FIG. 10 schematically illustrates a medial humeral fixation of the graft of FIGS. 8-9.

The graft 240 may be fixated both medially and laterally to the humerus 16. FIG. 10 schematically illustrates the medial humeral fixation of the graft 240 to the greater tuberosity 42 of the humerus 16. The location of the medial humeral fixation may occur at or near the cartilage margin of the superior capsular ligament 20. One or more suture anchors 264 may be used to medially fixate the graft 240. In an embodiment, the suture anchor 264 is a knotless suture anchor that knotlessly fixates one of the previously positioned sutures (here, suture 262D) to the humerus 16, thereby securing the graft 240 to the humerus 16 at the selected medial location. For example, the suture anchor 264 may wedge or trap the suture 262 between the anchor body and a sidewall that surrounds a socket 244 formed in the humerus 16 for receiving the suture anchor 264. Other types of suture anchors could alternatively or additionally be used to achieve the relative medial humeral fixation of the graft 240.

Figure 11:
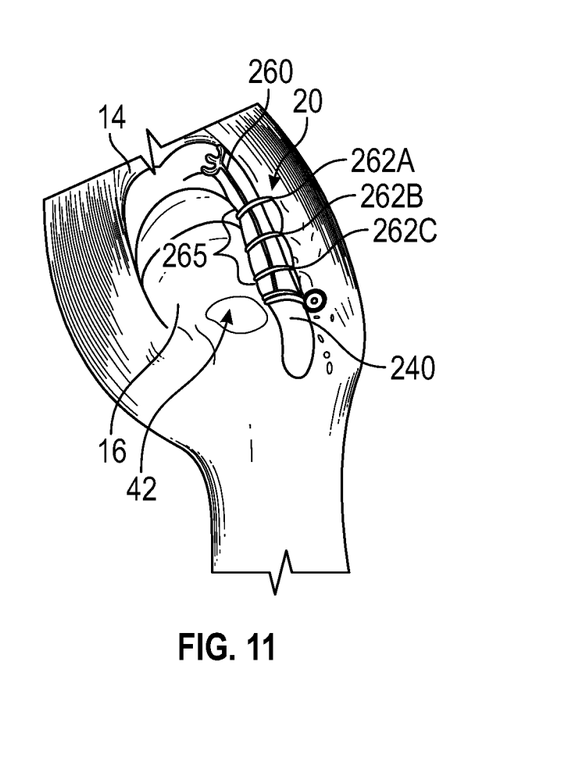
FIG. 11 schematically illustrates a side-to-side fixation of the graft of FIGS. 8-10.

The graft 240 may be further supported within the joint by utilizing a portion of the sutures (here, sutures 262A, 262B, and 262C) to provide side-to-side fixation of the graft 240 between the location of the medial fixation and the glenoid 14. An exemplary side-to-side fixation pattern 265 is illustrated in FIG. 11. In an embodiment, the sutures 262A, 262B, and 262C are knotless suture constructs that are passed through the superior capsular ligament 20, then passed around the graft 240, and then constricted to tighten the graft 240 between the graft 240 and the superior capsular ligament 20.

Figure 12A:
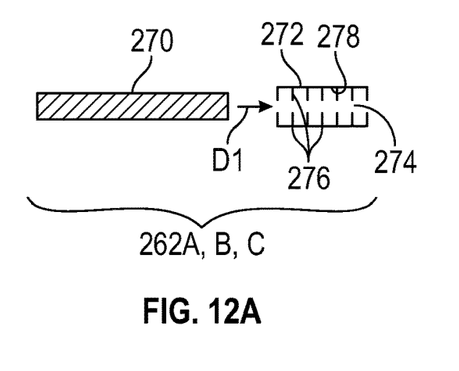
FIGS. 12A and 12B illustrate a knotless suture construct for use in preparing side-to-side suture fixation of the graft of FIGS. 8-11.
Figure 12B:
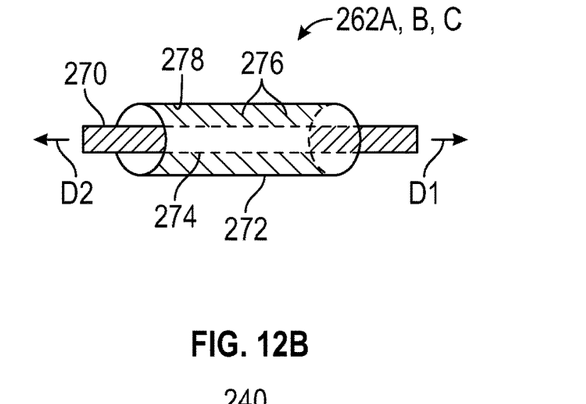

Each of the sutures 262A, 262B, and 262C may have a design similar to that shown in FIGS. 12A (exploded view) and 12B (assembly view). Each suture 262A, 262B, and 262C, for example, may include a suture strand 270 and a locking tube 272. The suture strand 270 may be inserted in a first direction D1 through a bore 274 of the locking tube 272. A plurality of fibers 276 protrude inwardly from an inner wall 278 of the locking tube 272. Once the suture strand 270 has been inserted in the first direction D1 through the bore 274 of the locking tube 272, the fibers 276 engage the suture strand 270 and prevent it from moving in a second direction D2 (i.e., opposite the first direction D1). This type of construct can be used to knotlessly fixate the graft 240.

In another embodiment, the medial fixation and side-to-side fixation of the graft 240 could be performed prior to harvesting the graft (e.g., prior to the tenotomy). This again illustrates that the order of steps of the exemplary reconstruction method is not intended to limit this disclosure.

Figure 13:
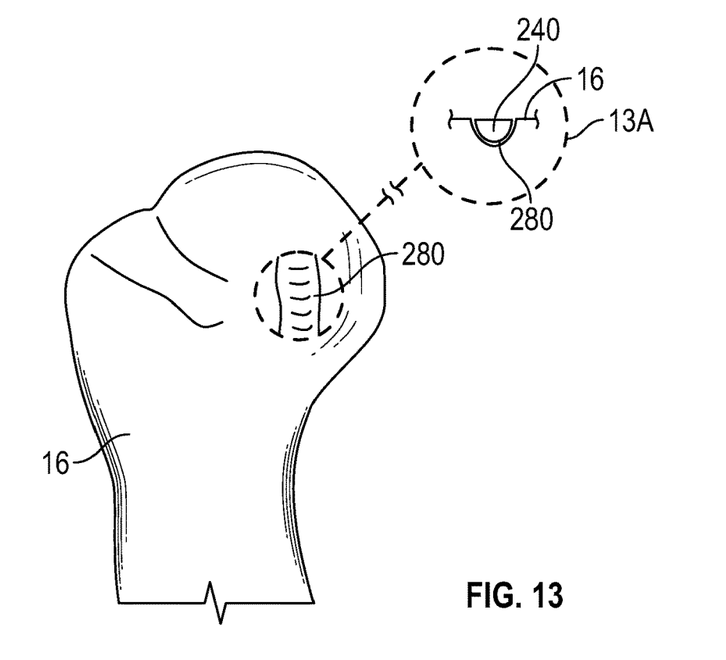
FIG. 13 schematically illustrates the formation of a trough in a humerus.

As illustrated in FIG. 13, a trough 280 may be formed in the humerus 16 for increasing the contact surface area and stability between the graft 240 and the humerus 16 (see inset 13A of FIG. 13). The graft 240 may be slightly recessed within the trough 280 relative to an outer surface of the humerus 16.

Figure 14A:
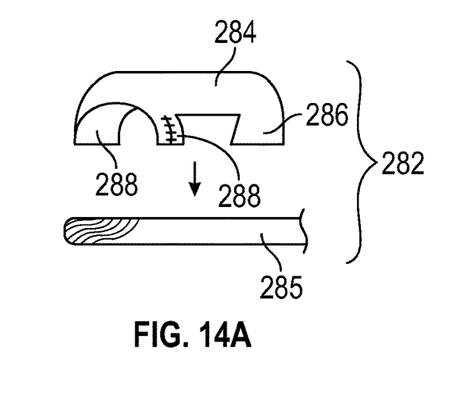
FIGS. 14A and 14B illustrate a burr and a detachable burr hood that can be utilized to form the trough of FIG. 13.
Figure 14B:
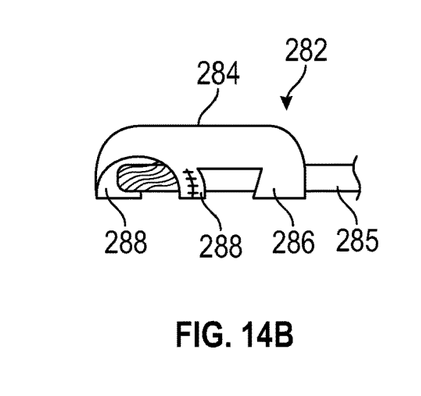

In an embodiment, the through 280 is formed using a surgical burr. An exemplary surgical burr 282 for forming the trough 280 of FIG. 13 is illustrated in FIGS. 14A and 14B. In this embodiment, the surgical burr 282 includes a detachable hood 284. The detachable hood 284 includes a clip 286 for snapping or sliding the detachable hood 284 onto a shaft 285 of the surgical burr 282. In an embodiment, the detachable hood 284 includes overhanging projections 288 that establish a depth stop of the surgical burr 282. For example, once the surgical burr 282 has reached a predefined cutting depth within bone, the overhanging projections 288 will contact the bone, thereby preventing further intrusion into the bone. Other surgical burrs could alternatively be used to form the trough 280 within the scope of this disclosure.

Figure 15:
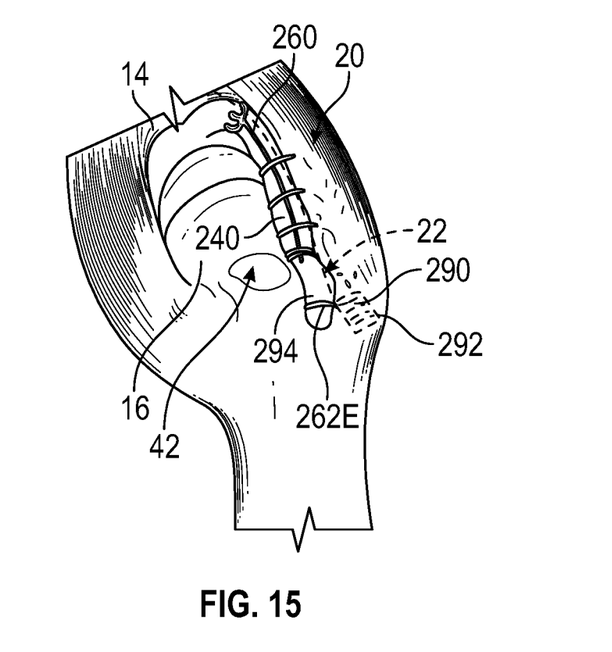
FIG. 15 schematically illustrates a lateral humeral fixation of the graft of FIGS. 8-11.

FIG. 15 illustrates the lateral humeral fixation of the graft 240 to the greater tuberosity 42 of the humerus 16. A suture anchor 290 may be secured in a socket 292 to tack down and stabilize a distal aspect 294 of the graft 240 to the greater tuberosity 42. In an embodiment, another suture 262E may be used in combination with the suture anchor 290 to achieve adequate fixation of the distal aspect 294. In this case, the suture 262E is passed through the distal aspect 294 of the graft 240 prior to connecting the suture 262E to the suture anchor 290 and inserting the suture anchor 290 into the socket 292. The suture anchor 290 could be a conventional suture anchor in which knots must be tied in the suture 262E to complete fixation or could be a knotless suture anchor that does not require knot tying. In another embodiment, the suture 262E may be looped around the distal aspect 294 rather than passed through the distal aspect 294.

Once fixated, the graft 240 extends along the anatomical attachment site of the native anterior cable region 22 (shown schematically with dashed line in FIG. 15). In other words, rather than reconstructing the entirety of the superior capsular ligament 20, the exemplary method reconstructs only the anterior cable region 22 of the superior capsular ligament 20 by localizing the graft 240 at an anatomical attachment site of the superior capsule on the greater tuberosity 42 of the humerus 16. Because the graft 240 is disassociated from the biceps muscle during resection, it functions solely as a ligament once fixated to the greater tuberosity 42. Thus, the graft 240 stabilizes the humerus 16 and the glenoid 14 relative to one another, thereby improving joint stability and kinematics. Therefore, once the rotator cuff is subsequently repaired, the rotator cuff may function solely as a tendon rather than both a tendon and a ligament. Because the tendon is both supported by the reconstruction and need not function as a ligament, the tendon repair may be maintained and sustained for a longer duration of time compared to a tendon repair that does not have such support or autologous bracing. The same applies for a tendon defect that has not undergone prior repair (e.g., irreparable rotator cuff tendon tear); the residual defect or remaining tendon is provided ligamentous support by the anterior cable reconstruction.

Figure 16:
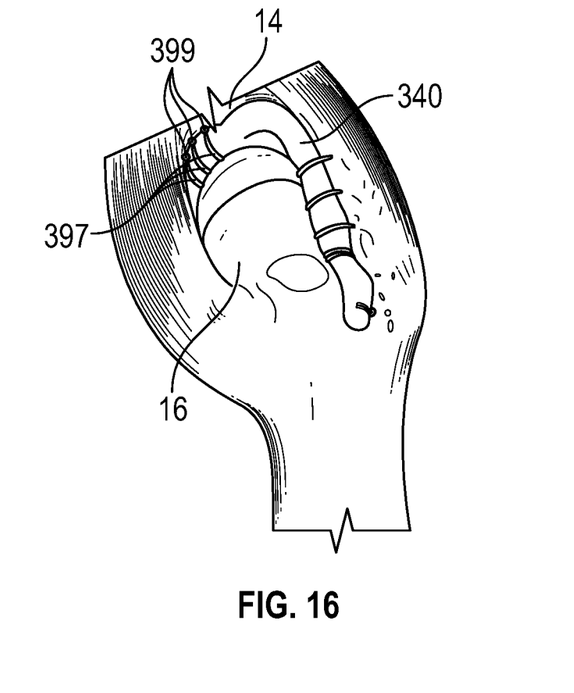
FIG. 16 schematically illustrates yet another exemplary method of reconstructing an anterior cable region of a glenohumeral superior capsular ligament.

FIG. 16 illustrates yet another exemplary method for reconstructing the anterior cable region of the superior capsular ligament. A graft 340 may be used to reconstruct the anterior cable region. In an embodiment, the graft 340 is an allograft such as a tibialis tendon, hamstring, or dermal allograft.

The graft 340 is attached on both the glenoid side and the humeral side of the glenohumeral joint 10. For example, the graft 340 may be affixed to the glenoid 14 using one or more sutures 397 and suture anchors 399. In an embodiment, the sutures 397 and suture anchors 399 are utilized to perform a Superior Labrum Anterior and Posterior (SLAP) to achieve glenoid fixation of the graft 340. Humeral fixation of the graft 340 can then be achieved in a manner similar to that shown in FIGS. 9-16 (i.e. medial, lateral, and side-to-side fixation).

A kit for performing joint kinematic reconstructions can also be provided. The kit may include, for example, the materials necessary for performing anterior cable region capsular reconstruction, or simply anterior cable reconstruction, in the manners shown and described with respect to FIGS. 8-16. In an embodiment, the kit includes:

1. One or more suture anchors for medial humeral fixation of an anterior cable region graft;
2. One or more suture anchors for lateral humeral fixation of the anterior cable region graft;
3. A plurality of sutures;
4. A surgical burr for forming a humeral trough; and
5. A cutting instrument for releasing the transverse ligament, such as during a biceps tendon tenotomy.

Optionally, the kit could include:
1. One or more knotless suture constructs/anchors; and
2. A detachable burr hood with depth stop for use with the surgical burr.

The anterior cable region reconstruction methods of this disclosure are designed to augment and brace or support rotator cuff repairs for non-end stage (i.e., repairable to any degree) rotator cuff tears or end-stage tears or defects (i.e., irreparable). Successful anterior cable region reconstructions allow subsequently repaired rotator cuffs to experience less stress and reduce injury recurrence by allowing the rotator cuff to function solely as a tendon rather than both a tendon and a ligament following the repair. The proposed methods additionally provide a novel technique for reconstructing only portions of capsular ligament as opposed to the entirety of the capsular ligament.

Although the different non-limiting embodiments are illustrated as having specific components, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should also be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method, comprising:
fixating a graft at a greater tuberosity of a humerus, wherein the graft is localized at an anterior cable region of a superior capsule of a glenohumeral joint, wherein fixating the graft improves tendon repair longevity and joint kinematics of the glenohumeral joint.

2. The method as recited in claim 1, wherein the graft is an autograft that is locally derived from a long head biceps tendon.

3. The method as recited in claim 2, comprising resecting the long head biceps tendon prior to fixating the graft.

4. The method as recited in claim 1, wherein fixating the graft includes inserting a suture anchor into the humerus to secure the graft to the greater tuberosity.

5. The method as recited in claim 1, wherein, upon fixation, the graft extends along an anterior region in relation to remaining rotator cuff tendon to a superior capsule attachment site region.

6. The method as recited in claim 1, wherein the graft is an allograft.

7. The method as recited in claim 6, comprising:
fixating the allograft at a region of a superior capsule attachment site with a first suture anchor; and
fixating the allograft at the greater tuberosity of the humerus with a second suture anchor.

8. The method as recited in claim 1, wherein reconstructing the anterior cable region includes repurposing an autologous tendon to act as a ligament for stabilizing the glenohumeral joint.

9. The method as recited in claim 8, wherein the autologous tendon is locally derived from a long head biceps tendon.

10. A method, comprising:
harvesting a graft from a long head biceps tendon, wherein the graft is harvested without detaching the long head biceps tendon from a superior glenoid attachment site of the long head biceps tendon; and
fixating the graft at a greater tuberosity of a humerus to stabilize a glenohumeral joint, wherein the graft is localized at an anterior cable region of a superior capsular ligament.

11. The method as recited in claim 10, wherein fixating the graft includes:
passing a suture through or around the graft;
forming a socket in the humerus; and
inserting a suture anchor into the socket to fixate the graft relative to the humerus.

12. The method as recited in claim 11, wherein the suture anchor is a knotless suture anchor.

13. The method as recited in claim 10, comprising, prior to fixating the graft:
reinforcing the graft with a reinforcement material.

14. The method as recited in claim 10, wherein fixating the graft includes:
securing the graft at a medial location of the humerus with a first suture anchor; and
securing the graft at a lateral location of the humerus with a second suture anchor.

15. The method as recited in claim 14, wherein fixating the graft includes:
securing the graft to an intact section of the superior capsular ligament with a plurality of sutures.

16. The method as recited in claim 15, wherein the plurality of sutures are arranged in a side-to-side fixation pattern.

17. The method as recited in claim 15, wherein at least one of the plurality of sutures is a knotless suture construct.

18. The method as recited in claim 10, comprising:
forming a trough in the humerus to increase a contact surface area between the graft and the humerus.

19. A kit for performing the anterior cable region reconstruction of the method of claim 10, comprising:
a first suture anchor for securing the graft at a medial humeral location;
a second suture anchor for securing the graft at a lateral humeral location, wherein at least one of the first suture anchor and the second suture anchor is a knotless suture anchor;
a plurality of sutures, wherein at least one of the plurality of sutures is a knotless suture construct;

a surgical burr configured for forming a trough in the humerus; and a cutting instrument configured for releasing the long head biceps tendon.

20. A method, comprising:

harvesting a graft, wherein the graft is an autograft; and fixating the graft at a greater tuberosity of a humerus to stabilize a glenohumeral joint, wherein the graft is localized at an anterior cable region of a superior capsule of the glenohumeral joint.

* * * * *